United States Patent
Lee et al.

(10) Patent No.: US 9,688,832 B2
(45) Date of Patent: Jun. 27, 2017

(54) METHOD FOR PREPARING MACROPOROUS POLYMETHYL METHACRYLATE

(71) Applicant: COSMAX CO., LTD., Hwaseong-si (KR)

(72) Inventors: Jun Bae Lee, Yongin-si (KR); Chun Ho Park, Yongin-si (KR); Hee Chang Ryoo, Seoul (KR)

(73) Assignee: COSMAX CO., LTD., Hwaseong-si (KR)

( * ) Notice: Subject to any disclaimer, the term of this patent is extended or adjusted under 35 U.S.C. 154(b) by 0 days.

(21) Appl. No.: 14/425,418

(22) PCT Filed: Mar. 18, 2014

(86) PCT No.: PCT/KR2014/002278
§ 371 (c)(1),
(2) Date: Mar. 3, 2015

(87) PCT Pub. No.: WO2014/163310
PCT Pub. Date: Oct. 9, 2014

(65) Prior Publication Data
US 2016/0009892 A1 Jan. 14, 2016

(30) Foreign Application Priority Data
Apr. 3, 2013 (KR) .................. 10-2013-0036219

(51) Int. Cl.
*C08J 9/28* (2006.01)
*C08F 20/10* (2006.01)
(Continued)

(52) U.S. Cl.
CPC ............. *C08J 9/286* (2013.01); *A61K 8/8152* (2013.01); *A61Q 19/00* (2013.01); *C08F 2/22* (2013.01);
(Continued)

(58) Field of Classification Search
CPC .................................................... C08J 2333/12
See application file for complete search history.

(56) References Cited

U.S. PATENT DOCUMENTS 3,505,434 A * 4/1970 Battaerd .................... B01J 2/00
264/15
5,662,938 A * 9/1997 Vert ....................... A61K 9/1647
264/4.6
(Continued)

FOREIGN PATENT DOCUMENTS

JP 2006241226 9/2006
JP 2009024067 2/2009
(Continued)

OTHER PUBLICATIONS

Wei, Q.; James, S.L. A metal-organic gel used as a template for a porous organic polymer. Chem. Commun., 2005, 1555-1556.*
(Continued)

*Primary Examiner* — Mike M Dollinger
*Assistant Examiner* — Christina Wales
(74) *Attorney, Agent, or Firm* — Cantor Colburn LLP (57) ABSTRACT

A method for preparing macroporous polymethyl methacrylate (PMMA) particles includes the steps of: (a) dissolving a polymethyl methacrylate polymer and Pluronic polymer into an organic solvent; (b) introducing the mixed solution of step (a) to an aqueous solution containing a surfactant to carry out emulsion polymerization; (c) heating the resultant product of step (b) to allow evaporation of the organic solvent; and (d) washing and drying the porous polymethyl methacrylate particles remaining after the evaporation.

7 Claims, 4 Drawing Sheets

(51) Int. Cl.
*C08F 2/22* (2006.01)
*A61Q 19/00* (2006.01)
*A61K 8/81* (2006.01)
*C08J 9/00* (2006.01)
*C08J 9/16* (2006.01)
C08J 3/09 (2006.01)
C08F 220/14 (2006.01)

(52) U.S. Cl.
CPC ............. C08F 20/10 (2013.01); C08J 9/0061 (2013.01); C08J 9/16 (2013.01); *A61K 2800/40* (2013.01); *C08F 220/14* (2013.01); *C08J 3/09* (2013.01); *C08J 2205/042* (2013.01); *C08J 2205/044* (2013.01); *C08J 2329/04* (2013.01); *C08J 2333/12* (2013.01); *C08J 2429/04* (2013.01); *C08J 2433/12* (2013.01); *C08J 2471/02* (2013.01)

(56) References Cited

U.S. PATENT DOCUMENTS

| 7,741,378 | B2 | 6/2010 | Cui | |
|---|---|---|---|---|
| 2007/0111002 | A1* | 5/2007 | Xia | .......................... C08F 6/14 428/407 |

FOREIGN PATENT DOCUMENTS

| KR | 1020060036614 | 5/2006 |
|---|---|---|
| KR | 1020070115913 | 12/2007 |
| KR | 1020110062708 | 6/2011 |

OTHER PUBLICATIONS

"Vortex-Genie 2 Shaker, 600 to 3200 rpm, 120 VAC" by Cole-Parmer Accessed at: http://www.coleparmer.com/Product/Vortex_Genie_2_Shaker_600_to_3200_rpm_120_VAC/EW-04724-00.*

Penzel, E. 2000. Polyacrylates. Ullmann's Encyclopedia of Industrial Chemistry.*

Sigma-Aldrich. Pluronic F-127.*

Nam, Y. S.; Park, T.G. Biodegradable polymeric microcellular formas my modified thermally induced phase separation method. Biomaterials, 20 (1999), 1783-1790.*

Qiang Wei and Stuart L. James. A metal-organic gel used as a template for a porous organic polymer. Chem. Commun., 2005, 1555-1556.*

International Search Report—PCT/KR2014/002278 dated Jun. 16, 2014.

Rong Zhang et al., Effect of Pluronic F127 on the pore structure of macrocellular biodegradable polylactide foams, Polymers for Advanced Technologies, 2004, pp. 425-430.

* cited by examiner

METHOD FOR PREPARING MACROPOROUS POLYMETHYL METHACRYLATE

TECHNICAL FIELD

The present invention relates to a method for preparing macroporous polymethyl methacrylate (PMMA). More particularly, the present invention relates to a method for preparing macroporous polymethyl methacrylate (PMMA) having high oil absorption by using a polymethyl methacrylate polymer and Pluronic polymer.

BACKGROUND ART

Polymethyl methacrylate (PMMA) is one of the polymerizates of methyl methacrylate. Polymerizates of methyl methacrylate are light and have high strength and excellent processability and durability, and thus are used widely in various industrial fields, including automobiles, wind screens for airplanes, optical products, displays, lighting instruments, cosmetics, pharmaceuticals, buildings, electric/electronic products, ornaments and general goods. In the cosmetic field, PMMA having a matte feel of use and high oil absorption is used widely for the production of fundamental cosmetics and make-up cosmetics. Particularly, powder including PMMA has high adsorbability to sebum, and thus is used widely for the production of fundamental cosmetics for controlling sebum and make-up cosmetics for modifying a skin color tone. However, since such powder mostly has a highly dense internal structure, there is a limitation in oil absorption. Therefore, a porous structure is required to improve oil absorption. For this, many attempts have been made to develop a porous type of powder. However, most porous powder materials used in the cosmetic field still have a highly dense internal structure and include fine pores with a size of several nanometers merely on the surface thereof. As a result, it is unsure whether such materials actually improve oil absorption or not.

The methods for preparing porous particles according to the related art include allowing a crosslinkable monomer and initiator to be absorbed and polymerized in polymer seed particles, or adding a mixture containing crosslinkable monomers to polymer microparticles and heating the resultant mixture in the presence of an oil-soluble initiator to the decomposition temperature of initiator to carry out polymerization.

Particularly, Korean Patent Laid-Open No. 10-2006-0036614 discloses a method for preparing porous polymethyl methacrylate. In the method, acrylic monomers and multifunctional monomers are polymerized by using a cosolvent formed of an organic solvent and an initiator, and then the cosolvent is removed from the resultant particles while forming nano-sized pores. In general, PMMA powder has an oil absorption of about 0.6 cc per gram. However, it is reported that the thus obtained porous PMMA powder having nano-sized pores has an oil absorption of about 1.8 cc/g to about 2.34 cc/g. In the method, as a cosolvent, an organic solvent such as toluene, n-hexanone, methyl isobutyl ketone or isoamyl alcohol is used. Thus, several times of washing are required undesirably in order to remove such an organic solvent.

In addition, the patent issued to Soken Chemical & Engineering Co., Ltd. (Japanese Patent Publication No. 2005-00055959, U.S. Pat. No. 7,741,378 and Korean Patent Laid-Open No. 10-2007-0115913) discloses porous monodispersed particles and method for production thereof. In the method, particles of polymethyl methacrylate or acrylic resin containing 70 wt % or more of methyl methacrylate as a copolymerizable component are used as seed particles, which, in turn, are swelled with a swelling solution containing at least 70 wt % of methyl methacrylate and 3-8 wt % of divinyl benzene and an oil-soluble polymerization initiator at a weight ratio of 20-80 times of the seed particles. After the swelling, polymerization is carried out to obtain porous particles. However, when preparing porous particles by using monomers and an initiator as mentioned above, the residue may have a negative effect. Thus, the above-mentioned manner of preparation of porous particles for use as a material for pharmaceuticals or cosmetics used directly in the human body not for industrial applications is always risky.

Under these circumstances, the present inventors have conducted many studies to overcome the above-mentioned problems occurring in the related art. As a result, we have found that porous polymethyl methacrylate obtained from a method for preparing macroporous polymethyl methacrylate (PMMA) by using a polymethyl methacrylate (PMMA) polymer and Pluronic polymer has high oil absorption and adsorbability to sebum, and thus it is effective for oil control when used for a fundamental cosmetic and make-up cosmetic composition, and has a low content of residual solvent and impurities, and shows a good feel of use and safety when applied to the skin.

DISCLOSURE

Technical Problem

A technical problem to be solved by the present invention is to provide a method for preparing macroporous polymethyl methacrylate (PMMA) having high oil absorption and a low content of residual solvent and impurities.

Another technical problem to be solved by the present invention is to provide a cosmetic composition of macroporous polymethyl methacrylate (PMMA) obtained by using the above method for preparing macroporous polymethyl methacrylate (PMMA).

Technical Solution

In one general aspect, there is provided a method for preparing macroporous polymethyl methacrylate (PMMA), including:

(a) dissolving a polymethyl methacrylate polymer and Pluronic polymer into an organic solvent;

(b) introducing the mixed solution of step (a) to an aqueous solution containing a surfactant to carry out emulsion polymerization;

(c) heating the resultant product of step (b) to allow evaporation of the organic solvent; and (d) washing and drying the porous polymethyl methacrylate particles remaining after the evaporation.

In the method, the mixed solution of step (a) containing a polymethyl methacrylate polymer and Pluronic polymer dissolved in methylene chloride is introduced to the aqueous solution containing a surfactant in step (b), and then emulsification is carried out, while the Pluronic polymer easily soluble in water moves toward the aqueous solution phase. This results in formation of a porous structure in the polymethyl methacrylate particles. In this manner, it is possible to obtain porous polymethyl methacrylate particles.

As used herein, Pluronic (Pluronic F-127) polymer is a non-ionic triblock heteropolymer and includes a central hydrophobic chain of polyoxypropylene and two lateral hydrophilic chains.

According to an embodiment, in step (a) of the method for preparing macroporous polymethyl methacrylate, the ratio of polymethyl methacrylate:Pluronic polymer may be 9:1-1:9, preferably 6:4-4:6.

According to the inventive Examples, when macroporous polymethyl methacrylate is prepared at a ratio of PMMA:Pluronic of 7:3, 6:4, 5:5 or 4:6, it is possible to obtain a good effect after the test.

According to the inventive Examples, as shown in Table 2, Example 1 shows the highest oil absorption, and oil absorption varies depending on the ratio of PMMA:Pluronic. However, in brief, the macroporous polymethyl methacrylate has a higher oil absorption as compared to the starting PMMA. This suggests that the macroporous polymethyl methacrylate having a different composition as disclosed herein has a higher oil absorption as compared to the conventional PMMA powder.

According to another embodiment, in step (a), any organic solvent capable of dissolving the polymethyl methacrylate and Pluronic polymer may be used. Preferably, the organic solvent may be selected from the group consisting of methylene chloride, n-hexanone, methyl isopropyl ketone, toluene and isoamyl alcohol.

According to still another embodiment, methylene chloride is used, since it easily evaporates at a relatively low temperature of 35-40° C. and is handled with ease. In the case of the other solvents, they have a relatively high boiling point and have a difficulty in removing the solvent. For example, the boiling points are as follows: n-hexanone (about 127° C.), methyl isopropyl ketone (about 94° C.), toluene (about 111° C.), and isoamyl alcohol (about 131° C.). Therefore, use of methylene chloride having a low boiling point is preferred in view of processability.

According to still another embodiment, in step (a), the organic solvent may be used in a ratio (w/v) of 0.01-1 g/mL based on the combined weight of the polymethyl methacrylate and Pluronic polymer.

Particularly, when the polymer is used at a low concentration, a large amount of organic solvent is used, and thus it is difficult to evaporate such a large amount of organic solvent. On the other hand, when the polymer is used at a high concentration of 1 g/mL or more, a relatively low amount of organic solvent is used, and thus the polymer cannot be dissolved sufficiently in the solvent and is present in an undesirably thick solution state. Once the polymer is dissolved totally into the solvent, the subsequent step of emulsification can be performed. If any polymer is not dissolved in the solvent but is present as it is, it is precipitated directly under the environment of aqueous solution during emulsification. As a result, it is not possible to obtain porous particles.

According to still another embodiment, in step (b), any surfactant may be used as long as it allows emulsification of the mixed solution obtained from step (a). Preferably, the surfactant may be at least one selected from the group consisting of polyvinyl alcohol, polyacrylic acid, vinyl acetate copolymer, ethyl cellulose, hydroxypropyl cellulose, polyvinyl pyrrolidone, polyvinyl methyl ether and polyethylene imine.

According to still another embodiment, in step (b), the surfactant may be used in an amount of 0.01-10.0 wt % (w/v) based on the volume of distilled water.

Particularly, the surfactant is related with the size of particles. As the concentration of surfactant increases, interfacial tension decreases and the surface area at the interface increases to generate a large amount of particles, resulting in a decrease in particle size. Therefore, such a decreased particle size also leads to a decrease in amount of Pluronic included in the particles, resulting in a decrease in pore size. On the contrary, as the concentration of surfactant decreases, particle size increases. Therefore, such an increased particle size also leads to an increase in amount of Pluronic included in the particles, resulting in an increase in size and number of pores.

According to still another embodiment, in step (b), the emulsification may be carried out under agitation at 1,000-10,000 rpm.

Particularly, the surfactant controls the size of particles depending on agitation speed. When the agitation speed increases, the emulsion system may be broken by high energy, while producing particles as small as possible. In this case, similarly to the case of surfactant, such a decreased particle size leads to a decrease in amount of Pluronic included in the particles, resulting in a decrease in pore size. On the contrary, when the agitation speed decreases, the emulsion system may be broken by low energy, while producing large particles. In this case, similarly to the case of surfactant, such an increased particle size leads to an increase in amount of Pluronic included in the particles, resulting in an increase in size and number of pores.

According to yet another embodiment, in step (d), the porous PMMA particles are washed with water to remove the Pluronic polymer remaining therein. Since the residual Pluronic causes degradation of a feel of use upon the application of a cosmetic product, it is preferred to minimize the residue. However, the Pluronic used herein is Pluronic F 127, a medical polymer approved by FDA (USA). Thus, even when the Pluronic remains in the porous PMMA particles, it may not adversely affect the human body.

In another aspect, there is provided a cosmetic composition including the macroporous polymethyl methacrylate obtained by the method as described above.

As used herein, 'macroporous polymethyl methacrylate' means porous particles having pores with a size of about 50 nm or more. Unlike the conventional porous particles having very fine pores with a size of several nanometers or less, such macroporous particles or macroporous powder refers to a pore size of at least 50 nm, preferably 50 nm-3000 nm. According to a particular embodiment, the macroporous particles have pores with a size of 200-1700 nm (0.2-1.7 µm).

According to an embodiment, the macroporous polymethyl methacrylate may have a particle size of 1-30 µm and pores with a size of 0.05-3 µm.

According to another embodiment, when the macroporous polymethyl methacrylate has a size smaller than the above-defined range, oil absorption decreases. On the other hand, when the macroporous polymethyl methacrylate has a size larger than the above-defined range, it is difficult for the polymethyl methacrylate to maintain its shape.

According to still another embodiment, the macroporous polymethyl methacrylate has an oil absorption of 1.0-5.0 cc/g.

According to some embodiments disclosed herein, as shown in Tables 2 and 3, the macroporous polymethyl methacrylate obtained by the above-described method has an oil absorption corresponding to at least 1.5 to 7 times of the oil absorption (0.65 cc/g) of PMMA before emulsification. As can be seen from such results, the macroporous polymethyl methacrylate obtained by the method disclosed herein has a higher oil absorption as compared to the conventional porous polymethyl methacrylate.

According to still another embodiment, the macroporous polymethyl methacrylate may be used as a formulation selected from the group consisting of milk lotion, cream, skin water, essence, pack, jelly, powder, lipstick, make-up base, foundation, lotion, ointment, gel, patch, cosmetic liquid, cleansing foam, cleansing cream, cleansing water, spray, shampoo, rinse, treatment, body cleanser, soap or other face cleansers.

According to the present invention, as shown in Tables 4 and 5, the test samples including the macroporous polymethyl methacrylate of the present invention show a skin oil content decreased by about 2.5 times as compared to the control including the conventionally used powder composition. This is because the porous particles of the present invention having a significantly high oil absorption as compared to the conventional porous particles absorb sebum appearing on the skin with the lapse of time after make-up, and thus are effective for oil control. As can be seen from the above results, the macroporous particles of the present invention are suitable for a cosmetic composition for the purpose of sebum control.

In addition to the above essential ingredient, the cosmetic agent according to the present invention may include other ingredients used currently in a cosmetic agent. Such ingredients include oil and fat ingredients, moisturizers, emollients, surfactants, organic and inorganic pigments, organic powder, UV absorbers, preservatives, sterilizers, antioxidants, plant extracts, pH modifiers, alcohols, colorants, fragrant, blood circulation stimulators, coolants, anti-perspirants, purified water, or the like.

The cosmetic composition according to the present invention may include effective ingredients used currently in cosmetic compositions, in addition to the extracts. For example, the cosmetic composition may include conventional supplementary ingredients such as stabilizers, solubilizers, vitamins, pigments and fragrant, and carriers.

Advantageous Effects

The porous polymethyl methacrylate obtained by the method according to the embodiments of the present invention has high oil absorption and a low content of residual solvent and impurities. Thus, when using the porous polymethyl methacrylate in fundamental cosmetics and make-up cosmetic composition, it shows excellent adsorbability to sebum and is effective for oil control. The porous polymethyl methacrylate also shows a good feel of use and is safe when applying to the skin.

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein.

Example 1: Preparation of Porous PMMA Particles

Figure 1:
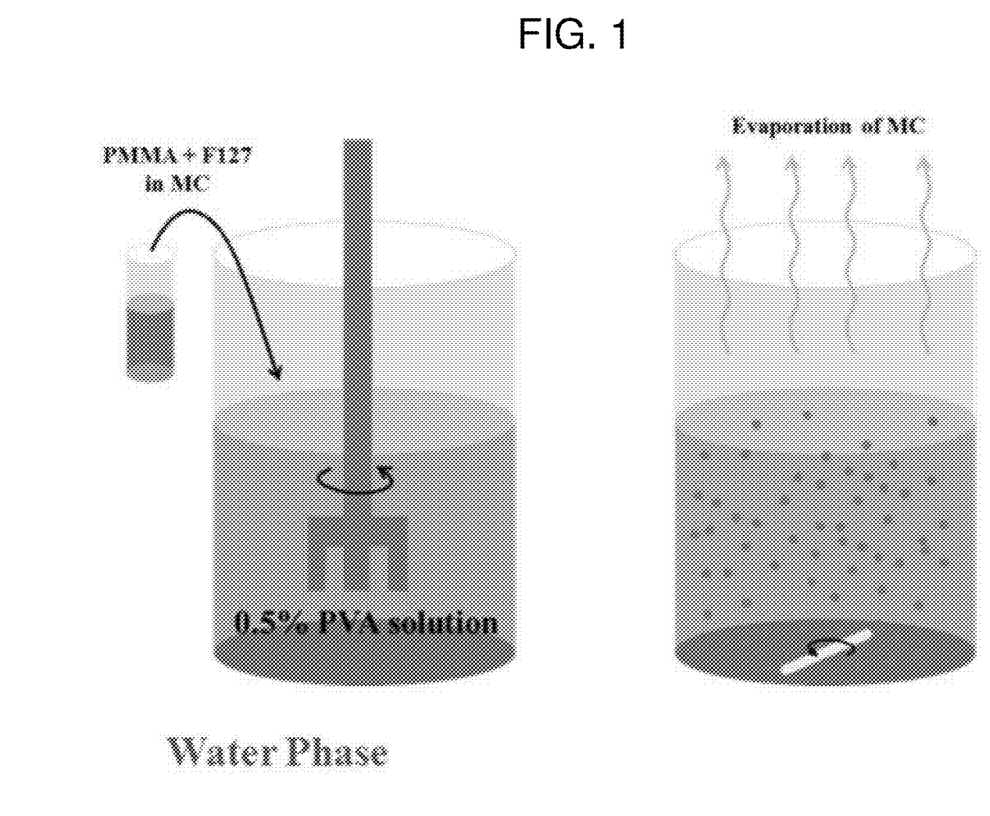
FIG. 1 is a schematic view illustrating a method for preparing macroporous polymethyl methacrylate (PMMA).

First, provided is 600 mL of 0.5% (w/v) aqueous surfactant solution of polyvinyl alcohol (PVA) (88% hydrolyzed, molecular weight: 146,000-186,000). Next, 20 mg of polymethyl methacrylate (PMMA, molecular weight 50,000) and 200 mg of Pluronic (Pluronic F-127) are introduced to a 20 mL beaker. Herein, the Pluronic denotes a triblock copolymer of ethylene oxide-propylene oxide-ethylene oxide. Then, 4 mL of methylene chloride (MC) is added thereto. The 20 mL beaker is covered with a lid, sealed with Teflon tape and agitated so that the reaction materials are dissolved completely. The resultant solution is introduced to a preliminarily prepared 0.5% (w/v) PVA solution and emulsification is carried out by using a homogenizer (high-speed agitator) at 5000 rpm for 10 minutes. The resultant emulsion is introduced to a beaker or crystallizing dish, transferred directly to a fume hood, and agitated at 37° C. under 300 rpm or higher for 3 hours to allow evaporation of the organic solvent. The emulsion is subjected to centrifugal separation under 1,000 g for 20 minutes. After the supernatant is removed, 10 mL of distilled water is added to carry out redispersion, and the resultant dispersion is introduced to a 50 mL tube. To remove Pluronic remaining in the tube containing the dispersion obtained by removing the supernatant after the centrifugal separation, 10 mL of distilled water is further added to carry out washing, and then the resultant product is added to the same 50 mL tube. Then, centrifugal separation is carried out at 1,000 g for 10 minutes. The supernatant is removed, and redispersion and washing are carried out by using 50 mL of distilled water. The washing procedure is repeated twice. The thus washed porous microparticles are subjected to freeze drying to remove water completely. The above procedure is shown in FIG. 1 in detail.

Example 2: Preparation of Porous PMMA Depending on Ratio of PMMA to Pluronic

Porous nanoparticles are provided in the same manner as Example 1, except that polymethyl methacrylate (PMMA, molecular weight 50,000) and Pluronic (Pluronic F-127) are introduced in an amount of 280 mg and 120 mg, respectively.

Example 3: Preparation of Porous PMMA Depending on Ratio of PMMA to Pluronic

Porous nanoparticles are provided in the same manner as Example 1, except that polymethyl methacrylate (PMMA, molecular weight 50,000) and Pluronic (Pluronic F-127) are introduced in an amount of 240 mg and 160 mg, respectively.

Example 4: Preparation of Porous PMMA Depending on Ratio of PMMA to Pluronic

Porous nanoparticles are provided in the same manner as Example 1, except that polymethyl methacrylate (PMMA, molecular weight 50,000) and Pluronic (Pluronic F-127) are introduced in an amount of 160 mg and 240 mg, respectively.

Example 5: Preparation of Porous PMMA Depending on Addition of Solvent (Methylene Chloride, MC)

Porous nanoparticles are provided in the same manner as Example 1, except that methylene chloride (MC) is used in an amount of 3 mL.

Example 6: Preparation of Porous PMMA Depending on Addition of Solvent (Methylene Chloride, MC)

Porous nanoparticles are provided in the same manner as Example 1, except that methylene chloride (MC) is used in an amount of 5 mL.

Example 7: Preparation of Porous PMMA Depending on Addition of Solvent (Methylene Chloride, MC)

Porous nanoparticles are provided in the same manner as Example 1, except that methylene chloride (MC) is used in an amount of 6 mL.

Test Example 1: Physical Properties of Porous PMMA Particles Depending on Ratio of PMMA to Pluronic PMMA particles are provided according to Example 1 to Example 4, and each type of particles is determined for the appearance, oil absorption and particle size. Based on the test results, the optimum proportion of polymer is determined. Then, the PMMA particles according to Example 5 to Example 7 are tested to determine the optimum content of methylene chloride (MC) used for emulsification considering the appearance, oil absorption and particle size.

The physical properties are determined as follows.

Appearance:

The porosity of particles is determined at the outer surface thereof by the naked eyes, and classified into grades of good, medium and bad. When the particles have high porosity at the outer surface thereof, they are classified into 'good'. When the particles have medium porosity and poor porosity, they are classified into 'medium' and 'bad', respectively.

Oil Absorption:

1 g of dried porous PMMA is weighed and put on an aluminum foil dish. Then, liquid paraffin is added dropwise thereto and the oil is mixed with powder to evaluate the oil absorption. The time point where the oil is not absorbed to the powder any more but is present as drops is taken as the end point. Oil absorption is measured five times, and the average and standard deviation are calculated.

Particle Size:

Scanning electron microscopy (SEM) is used to analyze particle sizes.

Pore Size:

The relative size of pores based on the scale bar in SEM is obtained by using the average and standard deviation.

Figure 2:
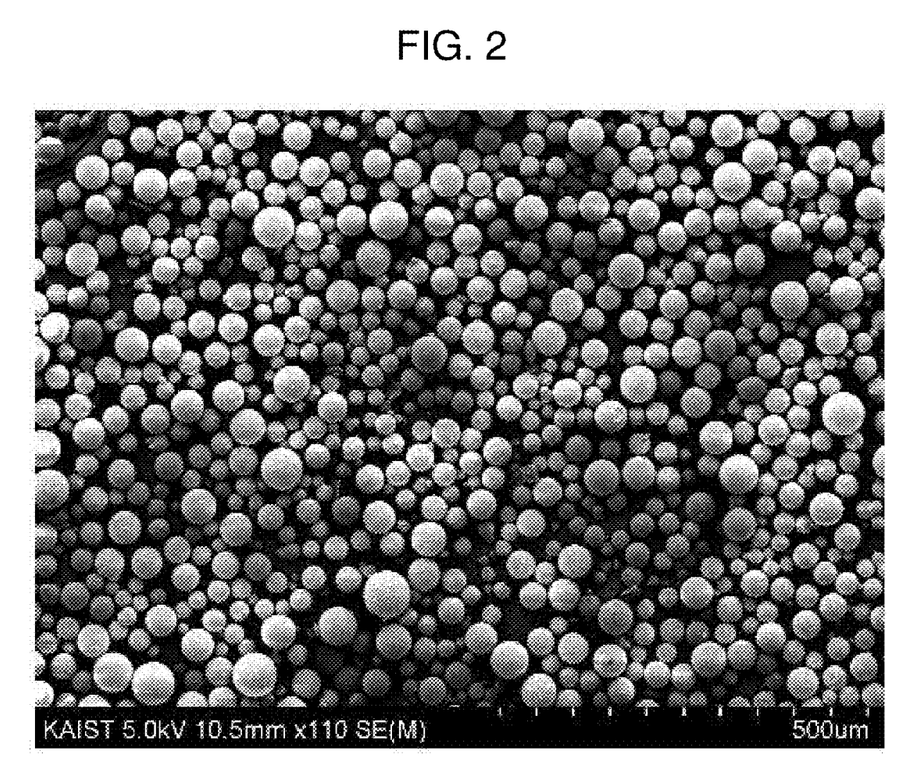
FIG. 2 shows the appearance of polymethyl methacrylate particles before emulsification.

The physical properties of the starting PMMA before emulsification are shown in Table 1. In Table 1, the appearance and particle size are observed and calculated based on the SEM image of FIG. 2.

TABLE 1

| | Appearance | Oil absorption (cc/g) | Particle size (μm) |
|---|---|---|---|
| Starting PMMA | Uniform appearance No porous structure | 0.65 cc/g (n = 5) | 10-50 |

Figure 3:
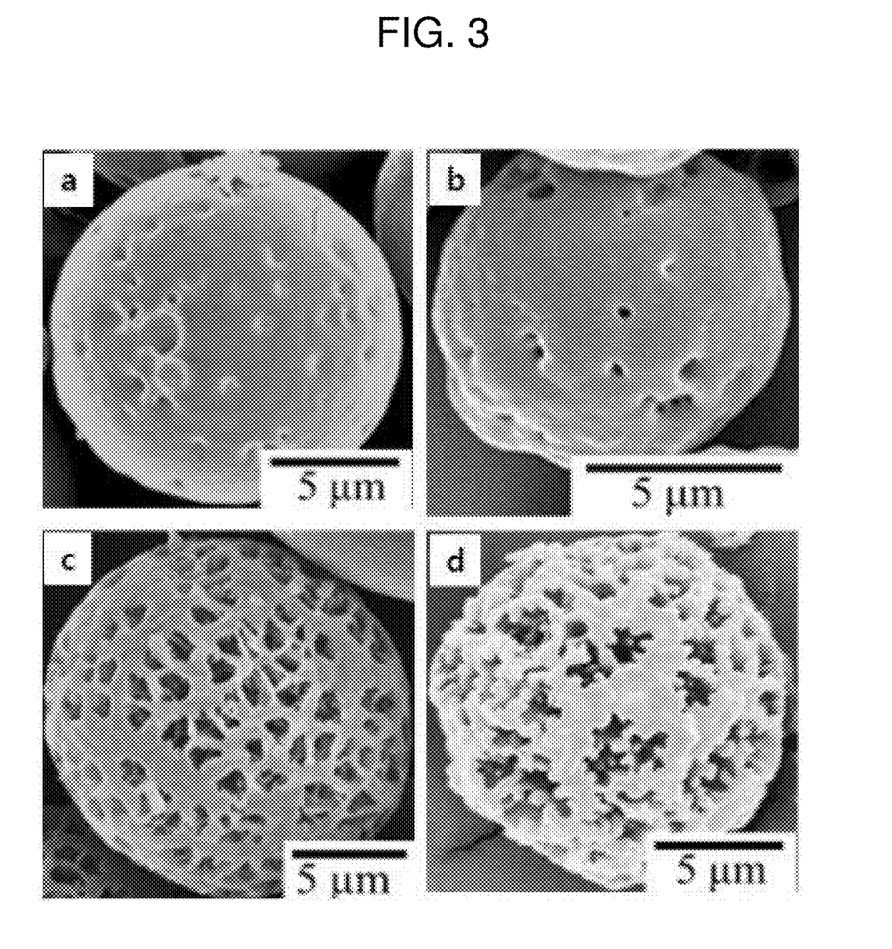
FIG. 3 shows the appearance of porous particles as a function of the weight ratio of PMMA to Pluronic F127 (a: Example 2, b: Example 3, c: Example 1, d: Example 4).

In addition, Table 2 shows the physical properties of porous PMMA as a function of the ratio of PMMA/Pluronic. The porous appearance, particle size and pore size are evaluated based on FIG. 3.

TABLE 2

| | PMMA/ Pluronic F127 weight ratio | Appearance | Oil absorption (cc/g) | Particle size (μm) | Pore size (nm) |
|---|---|---|---|---|---|
| Ex. 1 | 5/5 | Good | 4.24 ± 0.16 | 5-15 | 1323.5 ± 223.8 (n = 20) |
| Ex. 2 | 7/3 | Bad | 0.94 ± 0.09 | 5-15 | 285.7 ± 100.4 (n = 10) |
| Ex. 3 | 6/4 | Bad | 1.10 ± 0.13 | 5-15 | 218.8 ± 80.7 (n = 10) |
| Ex. 4 | 4/6 | Medium | 3.84 ± 0.13 | 5-15 | 1023.8 ± 115.0 (n = 20) |

As shown in Table 2, Example 1 shows a high oil absorption of about 4.2 cc/g and has a particle size of about 5-15 μm.

In addition, Example 1 has the largest pore size. It can be said that Example 1 having large pores shows high oil absorption. However, it is thought that such high oil absorption results from the uniformity and number of pores appearing on the surface and the characteristic internal structure rather than pore size. In fact, as can be seen from FIG. 3, Example 1 has a larger number of pores and more uniform pore pattern on the surface as compared to Example 4.

Figure 4:
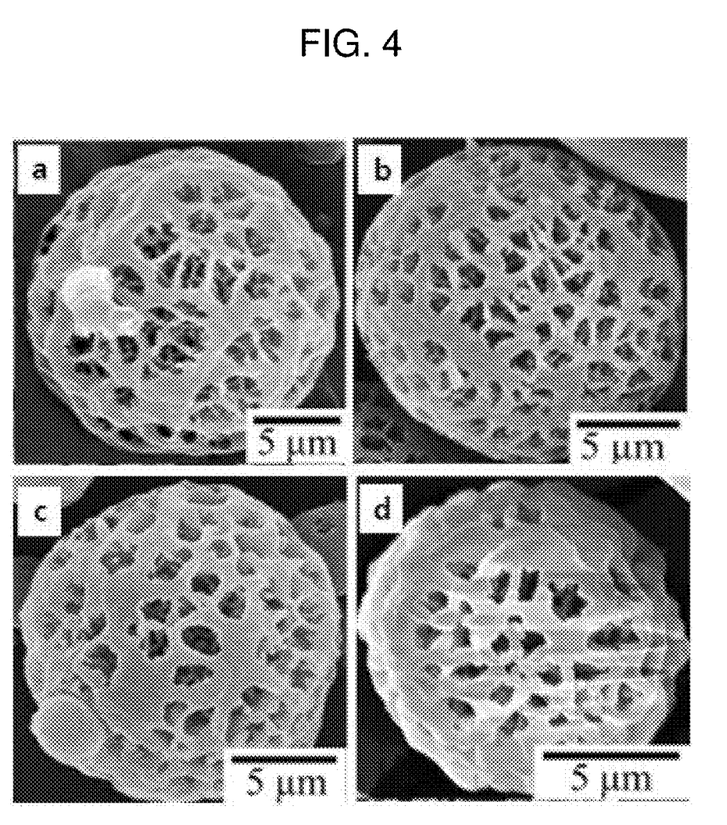
FIG. 4 shows the appearance of porous particles as a function of the volumetric content of solvent (a: Example 5, b: Example 1, c: Example 6, d: Example 7).

Further, the physical properties of porous PMMA particles as a function of the content of methylene chloride are shown in Table 3. The porous appearance, particle size and pore size are evaluated based on FIG. 4.

TABLE 3

| | MC content (mL) | Appearance | Oil absorption (cc/g) | Particle size (μm) | Pore size (nm) |
|---|---|---|---|---|---|
| Ex. 1 | 4 | Good | 4.24 ± 0.16 | 5-15 | 1323.5 ± 223.8 (n = 20) |
| Ex. 5 | 3 | Medium | 3.23 ± 0.10 | 5-15 | 1710.5 ± 248.9 (n = 20) |
| Ex. 6 | 5 | Medium | 3.40 ± 0.11 | 5-15 | 1578.9 ± 307.8 (n = 20) |
| Ex. 7 | 6 | Medium | 2.83 ± 0.11 | 5-15 | 989.1 ± 217.1 (n = 20) |

As shown in Table 3, the maximum value of oil absorption exists as a function of the content of methylene chloride (MC) as a solvent. In addition, when introducing an excessively large amount of solvent, no porosity is observed. In this test, the pore size of Example 5 or 6 is larger as compared to Example 1. However, it can be said that Example 1 has a larger number of pores and more uniform pores on the surface, and thus it shows a higher oil absorption.

Test Example 2: Determination of Oil Control
Effect of Porous PMMA

Example 1 that shows the highest oil absorption among Example 1 to Example 7 is tested for its oil control effect as compared to the starting PMMA.

TABLE 4

|  | Control | Test Sample |
|---|---|---|
| Talc (%) | 97 | 95 |
| Oil Binder (%) | 3 | 3 |
| Porous powder (Ex. 1) (%) | — | 2 |

Three healthy male adults participate in the test as subjects, and 7 mg of the sample prepared by using the composition of Table 4 is weighed precisely and applied to the forehead of each subject. Then, the amount of oil is measured with time and the average is calculated. The amount of oil is measured by using Sebumeter (Cosmomed, Germany).

TABLE 5

| Oil controllability (%) | 0 h | 1 h | 2 h | 4 h | 6 h |
|---|---|---|---|---|---|
| Control | 100 | 267 | 544 | 800 | 1556 |
| Test Sample | 100 | 269 | 375 | 581 | 644 |

The test results are shown in Table 5. The oil controllability as a function of time is shown by relative evaluation based on the initial amount of oil of each subject. After testing the oil controllability after 6 hours, the test sample containing 2% of Example 1 shows an effect about 2.5 times higher as compared to of the control.

The invention claimed is:

1. A method for preparing macroporous polymethyl methacrylate (PMMA) particles, comprising the steps of:
   (a) dissolving a polymethyl methacrylate polymer and a triblock copolymer of ethylene oxide-propylene oxide-ethylene oxide into an organic solvent;
   (b) introducing the mixed solution of step (a) to an aqueous solution containing a surfactant and mixing them to carry out emulsification;
   (c) heating the resultant product of step (b) to allow evaporation of the organic solvent; and
   (d) washing and drying the remaining product of step (c) to obtain the macroporous polymethyl methacrylate particles each having a plurality of macropores.

2. The method for preparing macroporous polymethyl methacrylate particles according to claim 1, wherein the polymethyl methacrylate polymer and the triblock copolymer are used in step (a) at a weight ratio of 9:1-1:9.

3. The method for preparing macroporous polymethyl methacrylate particles according to claim 1, wherein the organic solvent in step (a) is selected from the group consisting of methylene chloride, n-hexanone, methyl isopropyl ketone, toluene and isoamyl alcohol.

4. The method for preparing macroporous polymethyl methacrylate particles according to claim 1, wherein the organic solvent in step (a) is used at a ratio (w/v) of 0.01-1 g/mL based on a total weight of the polymethyl methacrylate and the triblock copolymer.

5. The method for preparing macroporous polymethyl methacrylate particles according to claim 1, wherein the surfactant in step (b) is at least one selected from the group consisting of polyvinyl alcohol, polyacrylic acid, vinyl acetate copolymer, ethyl cellulose, hydroxypropyl cellulose, polyvinyl pyrrolidone, polyvinyl methyl ether and polyethylene imine.

6. The method for preparing macroporous polymethyl methacrylate particles according to claim 1, wherein the surfactant in step (b) is used in an amount of 0.01-10.0 wt % (w/v) based on a volume of aqueous part in the aqueous solution.

7. The method for preparing macroporous polymethyl methacrylate particles according to claim 1, wherein the emulsification in step (b) is carried out under agitation at 1,000-10,000 rpm.

* * * * *